United States Patent [19]
Kayar et al.

[11] Patent Number: 5,630,410
[45] Date of Patent: May 20, 1997

[54] ACCELERATED GAS REMOVAL FROM DIVERS' TISSUES UTILIZING GAS METABOLIZING BACTERIA

[76] Inventors: Susan R. Kayar, 18739 Pier Point Pl., Gaithersburg, Md. 20879; Milton J. Axley, 14106 Heathfield Ct., Rockville, Md. 20853

[21] Appl. No.: 583,171

[22] Filed: Jan. 4, 1996

[51] Int. Cl.[6] ............ A61M 15/00; A62B 7/00; A01N 63/00; A61K 39/02
[52] U.S. Cl. ............ 128/200.24; 128/898; 424/93.4
[58] Field of Search ............ 128/200.24, 202.12, 128/202.13, 203.12, 203.15, 204.18, 205.26, 898; 424/93.4, 93.48, 94.6, 831

[56] References Cited

U.S. PATENT DOCUMENTS

| | | | |
|---|---|---|---|
| 4,035,479 | 7/1977 | George et al. | 424/78 |
| 5,356,625 | 10/1994 | Ying | 424/94.1 |
| 5,443,826 | 8/1995 | Brody et al. | 424/93.3 |

OTHER PUBLICATIONS

Layer & Groger, Digestion 54 (supplement 2):10–14 (1993).
Kumaroo & Imbert, NMRI report 90–61 public release AD–A226–476 Jul. 1990.
Keefe, et al., Archives of Biochemestry and Biophysics, vol 317, No. 2, Mar. 10, 449–456, 1995.
Axley et al., Advances in the Biosciences, vol 92, pp119–124, Elsevier, GB, 1994.
Abstract, Axley, International Society for the Use of Resealed Erythrocytes.

*Primary Examiner*—Kimberly L. Asher
*Attorney, Agent, or Firm*—A. D. Spevack, Esq.; William Garvert, Esq.

[57] ABSTRACT

Decompression from dives using nitrogen or hydrogen as a diluent gas are accelerated by introducing into the large intestine an enzyme or, preferably non-toxic bacteria from the group that metabolizes hydrogen or from the group that metabolizes nitrogen. The bacteria are encouraged to multiply and feed on the hydrogen or nitrogen (dependent on the gas mixture used in the dive) by metabolizing the diluent gas released into the large intestine and the new product is vented from the large intestine. The metabolism of the hydrogen or nitrogen causes a reduction of the partial pressure of the metabolized gas in the large intestine thereby increasing the diffusion of the metabolized gas from the blood and surrounding tissues into the intestine. The delivery of the bacteria is accomplished by any one of several means with packaging of the enzyme or bacteria in enteric coatings for oral ingestion as a prefered means.

9 Claims, 1 Drawing Sheet

ACCELERATED GAS REMOVAL FROM DIVERS' TISSUES UTILIZING GAS METABOLIZING BACTERIA

BACKGROUND OF THE INVENTION

1. Field of the Invention

This invention relates to a method for biochemical assistance in the decompression of divers using a breathing mixture of oxygen and a nitrogen or hydrogen gas diluent and a product for accomplishing the decompression. More particularly, this invention relates to a process for assisting in the removal of hydrogen gas ($H_2$) or nitrogen gas ($N_2$) from the systems of divers breathing $H_2$ or $N_2$ mixtures under hyperbaric conditions and a product for accomplishing decompression assistance. This product and method supplements and accelerates the removal of hydrogen and nitrogen gas that occurs spontaneously during conventional decompression of divers.

2. Description of the Prior Art

As soon as a diver submerges beneath the water, the diver begins to build a decompression debt. The debt is created by a greater mount of gases dissolving in the blood and cells as the greater depth causes an increase in the partial pressure relative to the conditions prevailing in 1 atm air. When the diver begins to return to the surface these gases leave solution and can create health and life threatening bubbles in the blood stream and tissues. The mount of dissolved gas in the blood and other tissues is a factor of time and pressure. The dissolution of this gas is not instantaneous but happens over time so, until equilibrium is reached, a shallow dive for a long period of lime can cause the dissolution of a substantially equal amount of gas as a deep dive for a short period of time. The limits to deep diving by humans are set by factors related to the increasing mass of the water column over the diver as the diver descends.

In order to ventilate the lungs during a dive, a gas mixture containing oxygen must be freely available to the diver at a pressure equal to that of the surrounding environment. This breathing gas cannot be pure oxygen ($O_2$). If the diver is to spend more than half an hour at a depth greater than 10 m, a pressure equal to 2 atmospheres, the diver might suffer from the cumulative toxic effects of $O_2$. At depths between 10 and 60 m, it is customary to dilute the $O_2$ with $N_2$ as in air. All references to gas mixtures with nitrogen are intended to include air. At depths greater than 60 m, helium is commonly used as the diluent because $N_2$ exerts narcotic effects at these pressures. However, at extreme depths in excess of 300 m, the density of a helium-$O_2$ breathing mixture is high enough to make it difficult for divers to ventilate their lungs comfortably, particularly during exercise. At depths greater than 300 m an $H_2$-$O_2$ gas mixture offers the advantage of lower gas density thereby providing a gas that is easier to breathe. An additional difficulty encountered at extreme depths is that divers often experience nausea, tremors, or seizures that appear to be induced by high pressure affecting nervous conduction, a phenomenon known as High Pressure Neurologic Syndrome (HPNS).

The diluent gas in the breathing mixture dissolves in the diver's tissues in proportion to the solubility of the gas in tissues and the partial pressure of the diluent gas. As the diver ascends and the partial pressure of the diluent gas decreases this causes a decreasing volume of gas to remain in solution in the tissues. The diver must ascend sufficiently slowly that the excess diluent gas can be eliminated via diffusion across the epidermal tissue, lungs, or other mucous membrane body surfaces, with the residual gas remaining in solution. If this ascent rate is exceeded, gas bubbles may form in the diver. When the gas bubbles are large and numerous, or in particularly vulnerable tissues such as the spinal cord and joints, they may cause a painful and potentially seriously debilitating condition known as decompression sickness (DCS).

The only method of decompression in current use is to carefully control the rate of a diver's ascent. The rate of ascent chosen is based on past history of ascent rates with minimal incidence of DCS. The earliest of these ascent charts were created by the United States Navy and are called the Navy diving tables. Recently, probabilistic models have been generated to assist this process of predicting safe ascent rates for a given dive. In the event that a diver experiences symptoms of DCS, the diver must be recompressed until the symptoms are relieved, and then decompression reinitiated more slowly, again according to past experience. Decompression is thus inherently dangerous because the diver's tissues must remain continuously in a supersaturated state in order to eliminate the burden of excess diluent gas. Decompression sickness cannot be predicted or prevented with absolute certainty became of its probabilistic nature and because each diver reacts differently. The same diver may have a different reaction at different times because of wellness factors. Therefore, the decompression rate necessary to prevent DCS for any individual can only be an approximation based on prior general experience because all the risk factors involved in the off-gassing rate for a given person are not and cannot be known.

Decompression can also be extremely time-consuming; it takes 12 days to safely decompress a diver from a 300 m dive that lasts as little as a few hours. During the ascent, the diver is at high risk of injury just dangling between the surface and the bottom. Thus, a method for shortening decompression would reduce a time of great personal risk to the diver as well as reducing expenses of the dive operation.

The concept of biochemical decompression was first proposed by Dr. Lutz Kiesow, who was a leading scientist in Diving Medicine at the Naval Medical Research Institute. Dr. Kiesow proposed using hydrogenase to cause biochemical decompression. According to this concept, a diver would breathe a gas mixture containing $H_2$ and $O_2$. The diver would be supplemented in some fashion with a hydrogenase enzyme, which is found in many bacteria. The hydrogenase enzyme would convert gaseous $H_2$ to some other molecule or molecules. This process would reduce the diver's burden of excess diluent gas as the diver ascended, thereby shortening the time needed to decompress safely. Dr. Kiesow did not specify any particular means of using the hydogenase or a situs for the interaction. Dr. Milton Axley tried to put this concept in action by trying to put the purified hydrogenase into the red blood cells themselves. Dr. Axley found he could encapsulate the enzyme into red blood cells, but could not devise an animal model in which to test the cells. This work is reported in part in an Abstract for the 5th Meeting of the International Society for the Use of Resealed Erythrocytes as ENCAPSULATION OF HYDOGENASE INTO RED BLOOD CELLS FOR THE PURPOSE OF BIOCHEMICAL DECOMPRESSION, Axley, Kayar, & Harabin 1993, article published in *Advances in the Biosciences*, Vol 92, pp119–124, 1994 (Elsevier). A study on the kinetics of the concept for use in blood was published as KINETIC MECHANISM STUDIES OF THE SOLUBLE HYDROGENASE FROM *ALCALIGENES EUTROPHUS* H16, by Keefe, Axley, & Harabin, Archives of Biochemistry and Biophysics, Vol 317, No. 2, pp 449–456, Mar. 10, 1995. The concept of incorporating the hydrogenuse into the blood was not further studied because even if the enzyme could be packed into the blood cells and be injected into a diver, the cells could only be circulated for a few weeks before the red blood cells died naturally and were eliminated through the spleen. The foreign protein of the injected enzyme could lead to splenic failure. There remains the concept of biochemical decompression, actually assistance to decompression because normal dissolution of gas continues to occur, without a means of effecting the biochemical decompression.

SUMMARY OF THE INVENTION

Accordingly, an object of this invention is to provide a method to increase the rate of removal of gaseous $H_2$ or $N_2$ from the tissues of divers breathing $H_2$ or $N_2$ gas mixtures during decompression.

Yet another object of the invention is to reduce the decompression time required of divers breathing $H_2$ or $N_2$ gas mixtures.

Another object of the invention is to reduce the deleterious side effects of hyperbaric conditions caused by excess gas dissolved in the tissues of divers breathing $H_2$ or $N_2$ gas mixtures.

These and additional objects of the invention are accomplished by introducing into the large intestine an enzyme or, preferably non-toxic bacteria selected from the group that metabolizes hydrogen or from the group that metabolizes nitrogen. The bacteria are encouraged to multiply and feed on the hydrogen or nitrogen (dependent on the gas mixture used in the dive) by metabolizing the diluent gas released into the large intestine, and the new product is vented from the large intestine. The metabolism of the hydrogen or nitrogen causes a reduction of the partial pressure of the metabolized gas in the large intestine thereby increasing the diffusion of the metabolized gas from the blood and surrounding tissues into the intestine. The delivery of the bacteria to the intestine is accomplished by any one of several means with packaging of the enzyme or bacteria in enteric coatings for oral ingestion that will protect the enzyme or bacteria while passing through the stomach but will dissolve and release the enzyme or bacteria by the time the package reaches large intestine.

More specifically, this invention relates to the development of bacteria that when delivered orally to a diver's large intestine during hyperbaric exposure to a gas mixture containing $H_2$ or $N_2$ metabolizes the $H_2$ or $N_2$ gas to other compounds such as methane or water for hydrogen and ammonia for nitrogen. In addition, this invention relates to the enteric coated product that delivers the enzyme or bacteria to the large intestine.

Other objects, advantages and novel features will be apparent to those familiar with the art upon reading the following detailed description of the invention.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures is diagrammatic and no attempt is made to indicate actual scales or precise ratios. Proportional relationships are shown as approximations.

DESCRIPTION OF THE PREFERRED EMBODIMENTS

Figure 1:
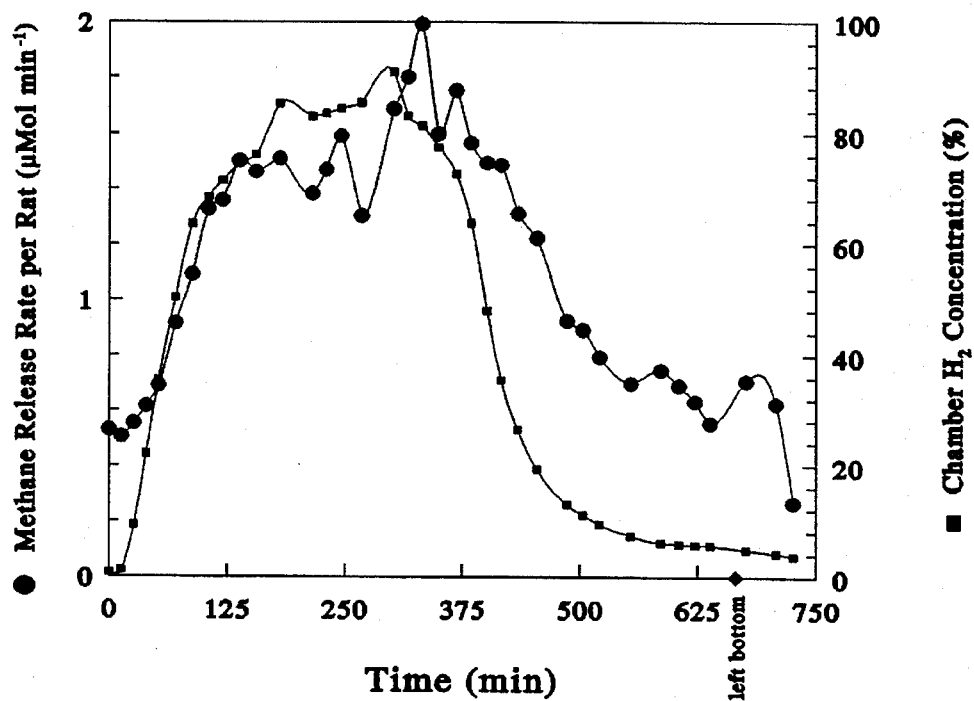
FIG. 1 is a graph of a dive with rats injected with *Methanobrevibacter smithii*. (330 fsw)

Since Dr. Kiesow first suggested that biochemical means should assist in decompressing a diver from a deep dive, researchers have explored various means to accomplish this objective. This invention relates to the finding that biochemical decompression, particularly from dives using hydrogen or nitrogen as the diluent gas for oxygen, can be confirmed by introducing either the enzyme itself or, more preferably, bacteria capable of metabolizing the diluent gas in the large intestine. The enzyme or bacteria metabolize the hydrogen or nitrogen gas present to either methane ($CH_4$) or ammonia ($NH_3$) respectively. Of course, the bacteria cannot be toxic to the host. In general, when hydrogen is the diluent, any hydrogen ($H_2$) and carbon dioxide ($CO_2$) metabolizing, methane-producing bacteria isolated from the intestinal tract of humans and other animals are useful for this invention. It is impossible to name all bacteria meeting this criteria because new ones are being isolated almost daily. Illustrative bacteria operable in this invention are *Methanobrevibacter ruminantium*, *Methanobrevibacter formicicum*, *Methanobrevibacter mobile*, *Anaerobrevibrio lipolytica*, *Vibrio succinogenes*, and *Acholeplasma bactoclasticum*. When the diluent gas is nitrogen, nitrogen fixing bacteria are the prefered agents. Nitrogen fixing bacteria belonging to the Family Enterobacteriaceae, which include 30 genera, are preferred. These bacteria must be species that use nitrogen gas as the nitrogen source. Examples of the genera containing species meeting the criteria are Rhizobium spp., Bradyrhizobium spp., Frankae spp. *Arsenophonus nasoniae*, *Budvicia aquatica*, *Edwardsiell tarda*, Enterobacter spp., Klebsiella spp. *Erwinia amylovora*, *Escherichia blatte*. Among these genera are species that are opportunistic pathogens which are eliminated as candidates or are altered to eliminate pathogenicity. Examples of pathogenic species not to be used are *Klebsiella pneumoniae*, and Salmonella spp.

Key to the invention is to deliver the bacteria (or for short dives, a specific quantity of enzyme can be used as an alternative) to the large intestine. This can be done via anal insertion (for laboratory animal) but the preferred route is by oral ingestion in the form of a delayed release capsule.

The preparation of delayed release capsiules that do not dissolve or release contents in stomach is well known. Such capsules are described in U.S. Pat. No. 3,074,852 where a cross-linked carboxy vinyl polymer carrier is intermixed with the bacteria. The enteric coating does not dissolve in the acid of the stomach but does, upon hydration, dissolve in the mildly alkaline conditions of the intestine. Other patents describing the preparation of enteric coated digestive enzyme compositions are U.S. Pat. Nos. 4,079,125 and 4,828,882.

The bacteria must be capable of returning to active metabolism. The bacteria can be included in the slow release capsule as a freeze dried product, as a cell paste preparation or in a gel formation in the same manner as Acidpohylus capsules now on the market. Exact dosages of bacteria will vary on the intestinal volume and the amount of gas which is expected to be processed.

In the preferred embodiment one or more capsules, tablets or other form of packaging containing the calculated dosage of bacteria is swallowed by the diver. In the preferred form the bacteria are freeze-dried encapsulation. The packaging must pass through the stomach and small intestine unharmed. The packaging begins to dissolve in the small intestine and is fully hydrated, and operational by the time it reaches the large intestine allowing them to colonize there indefinitely. It is necessary to provide sufficient lead time for the bacteria to reach and colonize the large intestine. On average, the capsule must be ingested about twelve hours before the bacteria are needed to assist in decompression. This invention demonstrates that $H_2$-metabolizing bacteria placed in the large intestines of rats do indeed eliminate $H_2$ dissolved in the rats' tissues, and that the rats' risk of decompression sickness (DCS) is subsequently lower. Hydrogen or nitrogen metabolizing bacteria placed in the large intestine of divers eliminate $H_2$ or $N_2$ dissolved in the divers tissues, resulting in a reduction of the risk of DCS.

When the diving gas mixture contains $H_2$ as a diluent to $O_2$, a culture of bacteria possessing an enzyme of the general class known as hydrogenase is introduced into the large intestine of the diver. This hydrogenase converts the $H_2$ to one of several possible other molecules, thus supplementing the rate of $H_2$ loss from the body as the diver is decompressed.

Biochemical Decompression with $H_2$ (a) Hydrogenase-containing Bacteria

Hydrogenases are protein enzymes that catalyze the metabolism of molecular $H_2$. These reactions are generally reversible; hydrogenase reactions can be made either to form or consume $H_2$. Many bacteria produce hydrogenase enzymes, and hydrogenase activities have also been detected in fungi, protists and plants.

All hydrogenase enzymes catalyze the oxidation of hydrogen as described in the reaction:

$$H_2 + X(ox) \rightleftharpoons X(red) + nH^+ \qquad \text{Equation (1)}$$

in which the oxidized form of an electron acceptor (X(ox)) accepts electrons removed from a molecule of hydrogen, and enters its reduced form (x(red)). The number of protons generated in the reaction (n) depends on the specific electron acceptor.

Methanogens are a general category of bacteria with hydrogenases that metabolize $H_2$ to form methane ($CH_4$). This reaction is:

$$4H_2 + CO_2 \rightleftharpoons CH_4 + 2 H_2O \qquad \text{Equation (2)}$$

As described above, there are more than 50 distinct species of methanogens, all of which are confined to environments without $O_2$. *Methanobrevibacter smithii* is an example of a methanogen that is particularly attractive for the purposes of biochemical decompression because this species is a common resident of the normal human gut flora. It has no known pathogenicity. As shown in Eq.2, *M. smithii* converts $H_2$ and $CO_2$ to methane and water, consuming 4 $H_2$ molecules for each molecule of methane produced. Under normal circumstances, the source of $H_2$ for this reaction is the end-product of fermentation by other bacteria in the intestine. People on a Western diet usually harbor only small populations of *M. smithii* and produce milliliter volumes of methane per day. However, some healthy individuals produce up to 4 liters of methane per day, thus metabolizing 16 liters of $H_2$. The methane passes harmlessly from the rectum.

Another example of a $H_2$-metabolizing bacterium that is suitable for our purposes is the soil bacterium *Alcaligenes eutrophus*. This bacterium produces both a soluble and an insoluble hydrogenase. The soluble hydrogenase is produced at extremely high levels of up to 0.5% of the total cell mass, and the bacterium can be easily grown in large quantities. It has no known pathogenicity.

The quantity of bacteria needed for this invention is a function of the specific activity of its hydrogenase; this varies greatly among bacteria. However, an estimate of the activity can be calculated, based on the volume of $H_2$ to be consumed and the length of time by which one would target to reduce the decompression time. These calculations can only provide an estimate because of many competing factors that can not be reduced to an absolute number. One such factor is that the diver continues to breathe the $H_2$ or $N_2$ diluted gas. It is assumed for the purpose of these calculations that the partial pressure of gas in the blood stream is supersaturated as the diver decompresses and no net additional gas will dissolve into the blood stream. Other factors can be ignored to provide an estimate. Total $H_2$ volume in a diver per unit body mass is a linear function of the partial pressure of $H_2$ to which the diver is exposed; the solubility of hydrogen at 37° C. is approximately 0.017 ml $H_2$ per gram muscle or blood plasma per atmosphere pressure. Thus, if a diver is at maximal depth and in steady state, i.e. saturated with hydrogen, and sufficient bacteria were present to consume 50% of the body burden of hydrogen over the same time interval at which 50% of their body burden of hydrogen would normally be offloaded by traditional decompression procedures, the overall speed of decompression would be doubled, and the time to decompress would be halved. A diver can be supplemented with greater quantities of bacteria, to remove even more $H_2$ per unit time.

The electron acceptor(s) used for the purposes of biochemical decompression are of equal importance to the hydrogenase reaction (Eq. 1); as a molecule of electron acceptor must be reductively consumed for every molecule of hydrogen. The amount of electron acceptor made available to a hydrogenase is the limiting factor regulating in vivo enzyme activity. A human diver weighing 70 kg, saturated at a pressure of 30 atm, would have approximately 1.5 moles of $H_2$ dissolved in his tissues. Therefore at least 1.5 moles of electron acceptor are required; 1.5 moles of NAD, the physiological electron acceptor of the soluble hydrogenase of *A. eutrophus*, weighs nearly one kilogram. This amount is difficult to deliver to divers during decompression.

The simplest solution to this problem is to use a hydrogenase reaction that requires an electron acceptor that is endogenous and readily regenerable under ordinary physiological conditions in the bacteria, or in the diver. The methanogen *M. smithii* uses $CO_2$ as its electron acceptor (Eq. 2). There is a large pool of $CO_2$ in the body as an end product of aerobic respiration, and as part of the bicarbonate buffer system that maintains normal physiological acid-base balance. Many bacteria in the intestine also produce $CO_2$ as an end product of their metabolism. The solubility of $CO_2$ in tissue fluids is about 30 times greater than the solubility of $H_2$. At the rate of $H_2$ metabolism that is needed for the purposes of biochemical decompression, it is not necessary to add supplemental $CO_2$.

(b) Location within the body

The bacteria must be introduced into the diver in a location to which $H_2$ can diffuse freely, and where the bacteria and any end products of the reaction will not cause major toxic effects or elicit an immune reaction. The only suitable body compartment is the large intestine. At the onset of a dive, or during decompression, the diver would swallow one or more capsules, tablets or other form of packaging containing the calculated dosage of bacteria. Preferably, the bacteria is freeze-dried or otherwise processed to withstand the encapsulation. As described above, the packaging allows the bacteria to pass through the stomach and small intestine unharmed. The packaging dissolves in the large intestine, liberating the bacteria and allowing them to colonize there indefinitely (but probably not permanently in significant numbers). This route of delivery of hydrogenase activity to the diver's body produces minimal immune or toxic reactions to a non-pathogenic bacterium or its metabolism in the intestine. The methane produced by the hydrogenase reaction is released harmlessly from the rectum as flatus, and the water also formed in this reaction is reabsorbed by the large intestine.

The intestine is also an ideal location for these strictly anaerobic bacteria because the large intestine is an anaerobic environment. Any traces of $O_2$ that diffuse into the large intestine are eliminated by the various species of intestinal bacteria that are facultative aerobes. Studies conducted as part of this invention show that $H_2$ diffusivity of the large intestines of rats has a $H_2$ diffusivity similar to that of dialysis tubing, a material that is routinely used in the laboratory for its high diffusivity to small molecules. The intestine is known to have a high mass-specific blood flow, and a major portion of the total cardiac output traverses the abdominal region. Thus the intestine is a suitable location for introducing hydrogenase because it is readily accessible to a large volume of the body's supply of $H_2$ during decompression.

When the diving gas mixture contains $N_2$ as the diluent, a culture of bacteria possessing an enzyme of the general class known as nitrogen-fixing enzyme is introduced into the intestine of the diver, for the same purpose of accelerating the loss of this gas during decompression.

Having described the invention, the following examples are given to illustrate specific applications of the invention including the best mode now known to perform the invention. These specific examples are not intended to limit the scope of the invention described in this application.

EXAMPLE 1

Experimental Model for $H_2$ Biochemical Decompression $H_2$ metabolism by *M. smithii* injected into the intestines of rats leads to a reduction in DCS incidence. Rats were placed in a box inside a dive chamber that was specially designed for operating with gas mixtures of $H_2$ and $O_2$. A stream of gas passing through the box was sampled by gas chromatography. Animals (n=20) that had not been injected with *M. smithii* released no detectable methane while breathing either helium (He) or $H_2$.

Two ml of a concentrated culture of *M. smithii* in a bicarbonate buffer were injected into the caecum (anterior end of large intestine) of rats, via a cannula introduced from the rectum. Animals (n=5) which were injected with bacteria were exposed to 11 atm (330 feet of sea water equivalent pressure) of a $H_2$-$O_2$ gas mixture. Methane release rate increased with increasing $H_2$ concentration in the chamber, to 2 µMol methane per minute for each animal, corresponding to a minimum $H_2$ consumption rate of 8 µMol $H_2$ per minute per animal (Eq.2). The $H_2$ in the chamber was then replaced again by helium, and methane production fell as the $H_2$ was eliminated (FIG. 1).

Figure 2:
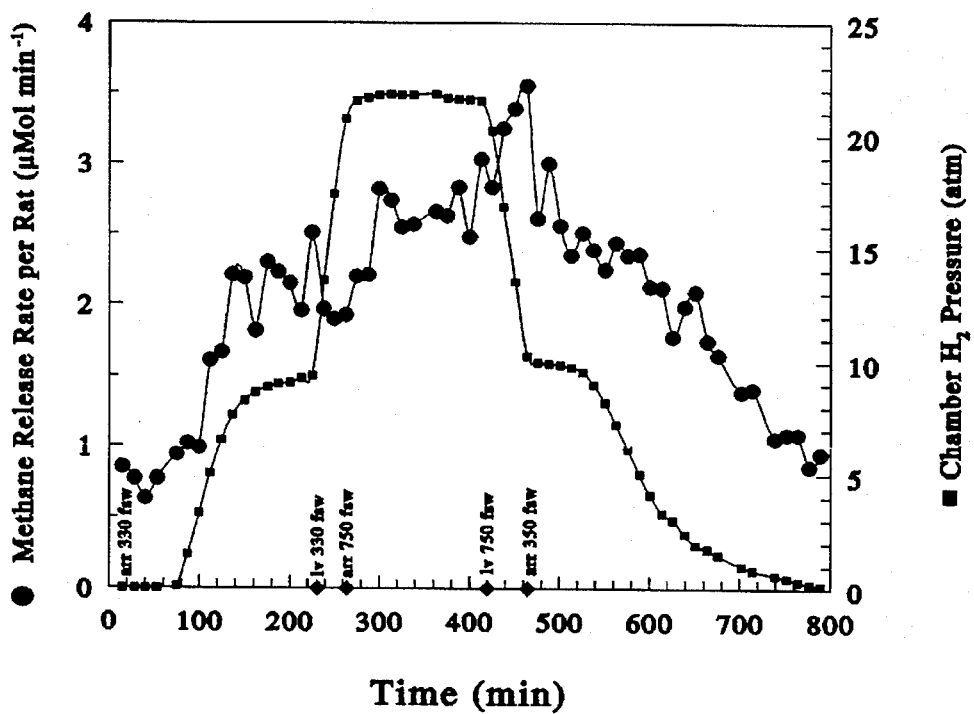
FIG. 2 is a graph of a dive with rats injected with *M. smithii*. (750 fsw)

A second group of 5 animals were injected with bacteria and exposed to a maximum pressure of 23.7 atm (750 fsw) of a $H_2$ and $O_2$ mixture. Methane release rate increased to 3.5 µMol per minute, corresponding to a minimum $H_2$ consumption rate of 14 µMol $H_2$ per minute per animal (Eq.2). The methane release rate fell again as the $H_2$ was eliminated from the dive chamber (FIG. 2). We assume that whenever $H_2$ is consumed and methane produced, some amount of the methane remains in solution in the animals and is not immediately detected, making the measured methane release rates only a lower estimate of the true $H_2$ consumption rate.

EXAMPLE 2

Model for DCS Incidence

Rats were enclosed in a slowly rotating treadmill which was positioned inside a dive chamber that was equipped with observation ports to permit continuous observation of the walking ability of the rats in a hyperbaric environment. The rats walked continuously while the chamber was pressurized to 23.7 atm at rate of 1–2 atm per minute with a breathing mixture of 2% $O_2$ in $H_2$. The rats were exposed to this pressure for 20 minutes to achieve saturation with $H_2$. The rats were then explosively decompressed to 11 atm and then monitored for 30 minutes for their physical responses. Limping, stumbling, and a general failure to keep up with the turning of the treadmill was observed in some animals. The observed symptoms experienced by the rats appeared to typical of DCS.

Many other dive profiles are also suitable, as well as other tests of DCS. The essential elements of the experimental model are that the incidence of DCS must be predictable in untreated animals, and that there be an objective test of the arthralgia, paralysis, numbness and loss of coordination associated with DCS.

Incidence of DCS was 20% (n=15 male rats, 275±4 g mean body mass) in animals injected with *M. smithii* and dived according to the profile described above. Animals that had received no bacterial injections had a DCS incidence of 57.5% (n=40, 259±5 g). Animals receiving caecal injections of bicarbonate buffer alone (n=20, 254±1 g), had a DCS incidence of 50.0%, demonstrating that the cannulation procedure did not affect DCS incidence. The incidence of DCS in animals treated with *M. smithii* was thus significantly lower (p=0.017, Fisher two-tailed exact test; p=0.013, Pearson Chi-square test) than that of control animals.

Calculations demonstrated that the lower DCS incidence in animals treated with *M. smithii* was attributable to biochemical decompression. We computed that decreasing the DCS incidence from 57.5% as in untreated control rats to 20% as found in those injected with bacteria, required an elimination of 370 µMol $H_2$. This calculation was based on previous knowledge of DCS incidence, of control rats at a variety of pressures (20% DCS risk occurs at 21.7 atm), and the solubility of $H_2$ in tissues (0.017 ml $H_2$/ml tissues per atm at 37° C.) of a rat weighing 275 g. At a minimum rate of 14 µMol $H_2$ consumption per minute by the bacteria, this amount of $H_2$ would be eliminated in 26 minutes. This time is within that allotted by the dive, before the normal onset of DCS symptoms.

The activity of hydrogenase introduced into these animals by injecting *M. smithii* was computed at 1 atm of pure $H_2$ to be 50 µMol $H_2$/min. This activity must be scaled down to the delivery rate of $H_2$ inside the animal, which is a function of the lower solubility of $H_2$ in tissue fluids than in the gas phase, and the diffusion rate of $H_2$ into the intestine from the surrounding tissues and blood. One milliliter of tissue fluids saturated with $H_2$ at a pressure of 23.7 atm of 98% $H_2$ contains only 40% of the $H_2$ contained in one milliliter of a bubble of pure $H_2$ at 1 atm. Thus, the maximal activity to be expected from our injection of *M. smithii* under these conditions was 0.4×50 µMol/min, or 20 µMol/min. There is thus an excellent correspondence between the activity of hydrogenase we introduced, the amount of $H_2$ metabolism actually occurring based on measured methane release rate (FIG. 2), and the amount of $H_2$ consumption we computed was necessary to reduce DCS by the amount we observed.

Animals injected with *M. smithii* and dived with $H_2$ appeared to be in normal health. Following the dive to test for DCS incidence, animals were euthanized inside the chamber for reasons related to chamber safety and to relieve any suffering from the few animals that experienced DCS. However, animals have been permitted to live for at least 48 hours following bacterial injection, with no apparent toxicity.

Biochemical Decompression with $N_2$

EXAMPLE 3

Bacteria that Fix $N_2$

The capacity to fix $N_2$ is often associated with hydrogenase activity. The general reaction believed to take place in $N_2$ fixation can be written as:

½ $N_2$+$H_2$+4ATP→⅔ $NH_3$+4ADP+4$P_i$ (Eq. 3)

The $N_2$ fixing bacterium *Klebsiella aerogenes* has been isolated from the feces of humans, pigs and guinea pigs. *K. aerogenes* is a Gram-negative, facultatively anaerobic rod type bacterium of the family Enterobacteriaceae. With nitrogen fixing bacteria, a boost is needed to "feed" the bacteria and spur the reaction. Glucose is an example of a suitable fuel source for this bacterium. Other sugars will work as well. Other enterobacteria found in human feces that also have $N_2$-fixing ability include *Enterobacter cloacae* and *Escherichia coli*. While many of the species in this family are pathogens, some are not. *K. aerogenes*, *E. cloacae* and *E. coli* are usually not pathogenic when confined to the intestine in small quantities, but may be opportunistic pathogens in wounds, the respiratory system, or other body locations. There are other nitrogen-fixing enterobacteria normally associated with plants that are non-pathogenic to humans and can also be used in this invention. The important consideration is that small populations of nitrogen-fixing bacteria normally inhabit the large intestine; this environment is thus clearly suitable for the short-term survival and metabolism of nitrogen-fixing bacteria. Non-pathogenic species can be identified with applied research using known methods.

As in the ease of $H_2$, the amount of bacteria needed to eliminate sufficient volumes of $N_2$ for decompression purposes is a function of the nitrogen-fixing activity of the particular species of bacterium used. Given the biological link between nitrogen fixation and hydrogenase activity, it is assumed that similar relative activity levels can be obtained in the two cases. Since $N_2$ is used as a diving gas only at shallow depths of 200 fsw (7 atm) or less, far less $N_2$-fixing ability is needed than is needed for $H_2$ biochemical decompression because a relatively small volume of $N_2$ is in excess. However, the small amount of $N_2$ in solution will also make enzymatic rate low.

$N_2$ has a slightly lower solubility (0.014 ml $N_2$/ml tissue fluids) than $H_2$. If we supply enough nitrogen-fixing activity for 50 µMol $N_2$/min in vitro as we did for $H_2$ above, we can expect to actually eliminate up to 4 µMol $N_2$/min in vivo by biochemical means, after correcting for the solubility of $N_2$ in a rat saturated with air at 200 fsw. Total excess $N_2$ load in this rat is 950 µMol $N_2$ (0.014 ml $N_2$/g×275 g×6.3 atm×273°/310° K.×1 mmol/22.4 ml). The current estimate of $N_2$ elimination time from a rat by diffusion alone from this dive is 75 minutes, based on previous dive studies. Thus diffusion alone occurs at an average rate of approximately 12 µMol $N_2$/min. If enzymatic means are used to eliminate additional $N_2$ at a rate of 4 µMol $N_2$/min, then the length of time spent eliminating gases can be shortened by at least one third. Sample calculations with human dive profiles with $N_2$ yield similar results.

Location within the body

The $N_2$-metabolizing bacteria are highly anaerobic, making the large intestine the ideal, and in fact the only location suitable for the purposes of biochemical decompression. An expected end product of ammonia from their metabolism is not likely to be a limitation as it would be in any other location within a mammal. Ammonia is abundant in the large intestine as an end product of protein digestion, and numerous species of intestinal bacteria consume ammonia as their primary nitrogen source. Other end products of nitrogen-fixation may be nitrites or nitrates, which also are readily taken up by other intestinal bacteria for their own metabolism.

Experimental model for $N_2$ biochemical decompression

The experimental model to demonstrate $N_2$ biochemical decompression and reduction in DCS incidence for animals treated with $N_2$-fixing bacteria is similar to the model for $H_2$ biochemical decompression. A sample dive profile is selected with a known incidence following the same dive profile.

Thus, $N_2$ biochemical decompression takes place by presentation of $N_2$-fixing bacteria in a manner analogous to that of $H_2$ metabolism. Them are additional steps involved for $N_2$, as for example adding a fuel source for the bacteria, or genetically altering the bacteria to make them use molecular $N_2$ as a nitrogen source. Non-pathogenic nitrogen-fixing bacteria are identified, processed, and packaged for oral delivery to the large intestines of humans as described for $H_2$ biochemical decompression.

Many modifications and variations of the present invention are possible in light of the above teachings. It is therefore to be understood that, within the scope of the appended claims, the invention may be practiced otherwise than as specifically described.

What is claimed is:

1. A method of accelerating decompression of a diver decompressing from a dive while breathing a mixture of an $H_2$ or $N_2$ diluent and $O_2$, comprising the steps of:
   a. Introducing bacteria selected from the group consisting of hydrogenase possessing bacteria and nitrogen-fixing bacteria into the large intestine;
   b. Permitting said bacteria to colonize the large intestine; and
   c. metabolizing said $H_2$ or $N_2$, whereby the rate of elimination of $H_2$ or $N_2$ from a diver's tissues is accelerated with no serious side, toxic or immunological effects.

2. The method of claim 1, wherein the hydrogen or nitrogen bacteria is delivered orally and passes through an individual's stomach, small intestine, and into said large intestine before being released.

3. The method of claim 2, wherein said metabolism is aided by a fuel source, said fuel source selected from the group consisting of sugars and high energy phosphates.

4. The method of claim 1, wherein the bacteria are hydrogenase bacteria.

5. The method of claim 4, wherein said hydrogenase possessing bacteria is selected from the group consisting of *M. smithii* and *Alcaligenes eutrophus*.

6. The method of claim 4, wherein said bacteria is disposed in a package comprising an enteric coated slow release container.

7. The method of claim 5, wherein said bacteria is disposed in a package comprising an enteric coated slow release container.

8. The method of claim 1, wherein said bacteria are nitrogen-fixing bacteria.

9. The method of claim 8 wherein said nitrogen-fixing bacteria are selected from the group consisting of *Klebsiella aerogenes, Enterobacter cloacae,* and *Escherichia coli.*

* * * * *